(12) United States Patent
Kesling

(10) Patent No.: US 7,581,950 B1
(45) Date of Patent: Sep. 1, 2009

(54) ORTHODONTIC APPLIANCE

(76) Inventor: Andrew C. Kesling, 1753 S. 100 W., LaPorte, IN (US) 46350

( * ) Notice: Subject to any disclaimer, the term of this patent is extended or adjusted under 35 U.S.C. 154(b) by 95 days.

(21) Appl. No.: 11/018,153

(22) Filed: Dec. 20, 2004

(51) Int. Cl.
*A61C 3/00* (2006.01)
(52) U.S. Cl. .............................. 433/8; 433/9
(58) Field of Classification Search .............. 433/8–18, 433/21
See application file for complete search history.

(56) References Cited

U.S. PATENT DOCUMENTS

| | | | |
|---|---|---|---|
| 2,196,516 A | | 4/1940 | Atkinson |
| 4,842,512 A | | 6/1989 | Kesling |
| 4,842,514 A | | 6/1989 | Kesling |
| 4,859,179 A | * | 8/1989 | Kesling ......................... 433/8 |
| 4,877,398 A | | 10/1989 | Kesling |
| 5,125,832 A | | 6/1992 | Kesling |
| 5,271,733 A | * | 12/1993 | Chikami et al. ................ 433/20 |
| 5,890,892 A | * | 4/1999 | Lemchen ........................ 433/9 |
| 6,682,345 B2 | | 1/2004 | Kesling et al. |
| 6,685,468 B1 | * | 2/2004 | Kesling .......................... 433/9 |
| 2003/0180678 A1 | * | 9/2003 | Kesling et al. ................. 433/8 |

* cited by examiner

*Primary Examiner*—John J Wilson
(74) *Attorney, Agent, or Firm*—Lloyd L. Zickert

(57) ABSTRACT

An orthodontic appliance, and more particularly an orthodontic bracket to be used in conjunction with other brackets on centrals, laterals, cuspids and bicuspids for moving teeth in the orthodontic treatment of patients, and which includes a closed archwire slot that preferably functions to allow crown tipping, limiting root uprighting, and controlling torque, and a horizontally open rectangular archwire slot for controlling tip, torque and rotation in the final stage of patient treatment. The bracket is made by configuring a front section having a horizontally open rectangular archwire slot of metal, ceramic or plastic, and molding a rear or back section of a suitable plastic resin onto the front section such that the rear section preferably includes a closed mesiodistally extending archwire slot.

19 Claims, 4 Drawing Sheets

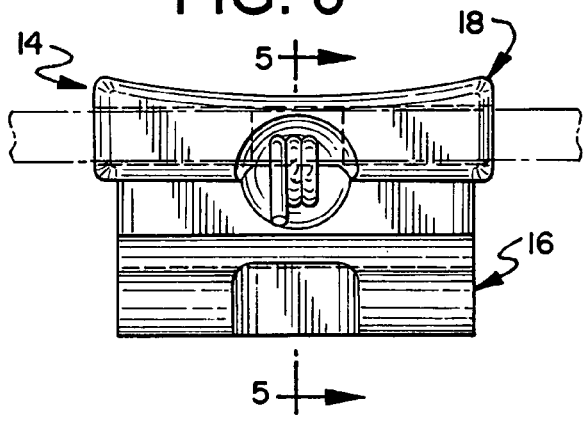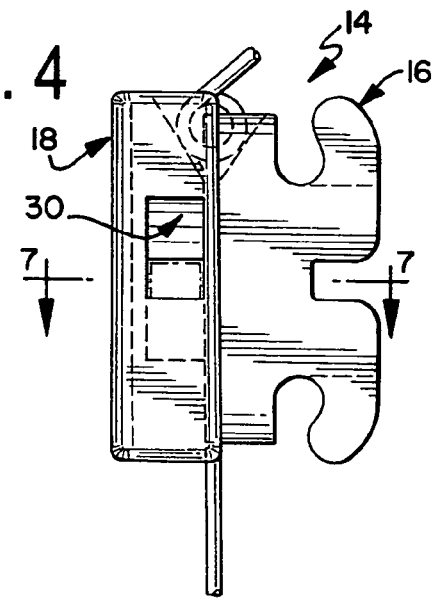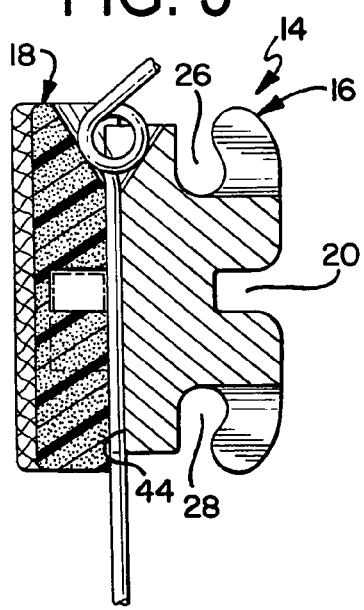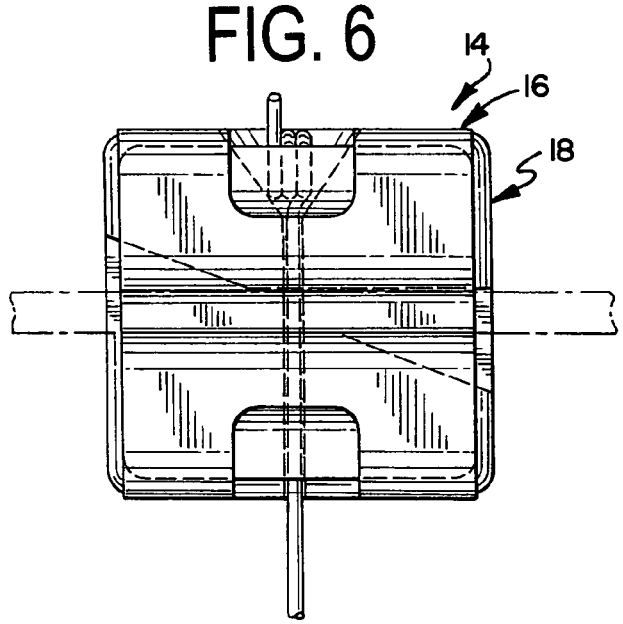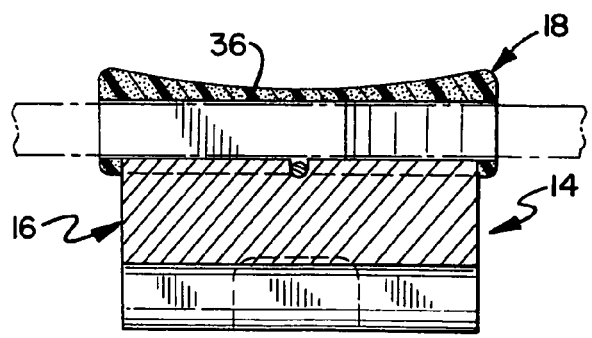

ORTHODONTIC APPLIANCE

This invention relates in general to a new and improved orthodontic appliance for orthodontically treating a patient, and more particularly to a new and improved bracket that may be used in combination with other brackets and appliances which includes multiple archwire slots, and still more particularly to a new and improved bracket having a closed archwire slot preferably functioning to allow crown tipping, limit root uprighting and controlling torque, and a horizontally open rectangular archwire slot for controlling tip, torque and rotation.

BACKGROUND OF THE INVENTION

Heretofore, it has been well known to provide orthodontic brackets having multiple archwire slots for receiving archwires and particularly archwire slots that are open for receiving rectangular archwires for the use in treating patients with the edgewise technique and slots for receiving archwires in the treatment of patients during the Begg or light wire technique, such as shown in U.S. Pat. No. 2,196,516.

It has also been well known to provide orthodontic brackets having means for accommodating crown tipping, root uprighting, and torquing functions, such as disclosed in U.S. Pat. Nos. 4,877,398 and 5,125,832. Brackets of this type are viewed as having a Tip Edge® slot for practicing the Tip Edge® technique. Tip Edge® is a registered trademark owned by TP Orthodontics, Inc. of Westville, Ind. While the brackets in these patents have been designed for using round or rectangular wire, they particularly perform torquing functions with rectangular wire and allow the movement of teeth along the archwire and the arch.

Further, the brackets disclosed in the above patents include vertically extending slots or openings for receiving the tails of uprighting springs to perform a root uprighting function where desired. Additionally, U.S. Pat. No. 4,842,514 discloses a type of uprighting spring that may be used with brackets having vertical openings.

It has also been known to provide an orthodontic bracket having a pair of contiguous labiobuccally opening archwire slots, one of which allows tipping and uprighting movement, and the other of which provides torquing movement, as shown in U.S. Pat. No. 4,842,512. It has also been known to provide a bracket having a pair of contiguous archwire slots which allows crown tipping, limits root uprighting, and controls torquing, while the other slots functions to stabilize tooth movement in three dimensions as sold by TP Orthodontics, Inc. of Westville, Ind., and illustrated in TP's 1998 product catalog on page 32.

Moreover, it has been known to provide an orthodontic bracket including a main archwire slot that allows crown tipping, root uprighting, and torquing functions, and additionally a lumen or tunnel which produces a final uprighting function with the use of a highly flexible archwire without the use of individual uprighting springs, as shown in U.S. Pat. No. 6,682,345.

SUMMARY OF THE INVENTION

The present invention relates to an orthodontic appliance, and particularly an orthodontic bracket, including a horizontally opening rectangular archwire slot to receive a rectangular archwire for treating patients under the edgewise or straight-wire technique, a closed archwire slot having means coacting with an archwire to treat patients with the Tip Edge® technique, and a vertical slot for accommodating an uprighting spring to produce uprighting forces. A recess is provided for allowing part or all of the uprighting spring head to be received and essentially become invisible from the labial or front of the bracket for enhancing the cosmetics of the brackets.

Thus, the bracket of the invention gives an orthodontic practitioner the option to use a closed archwire slot to orthodontically treat malpositioned teeth and particularly for easily moving teeth along an arch by employing the Tip Edge® technique, as well as providing a horizontally opening rectangular slot for receiving a main aligning archwire particularly during the final stages of orthodontic treatment when employing the edgewise or straight-wire technique. The bracket of the invention also includes a vertical slot for accommodating the use of an uprighting spring to give the orthodontic practitioner the option of using such a spring where uprighting of teeth is desired.

Additionally, the bracket of the invention consists of a front part which is configured to provide a horizontally open rectangular archwire slot, and a rear or back part of a plastic resin molded to the front part and configured to provide a closed mesiodistally extending archwire slot preferably for employing the Tip Edge® technique. The front section may be of any desired material, such as stainless steel or another metal, ceramic, or plastic, while the molded rear section may be of an acrylic of a suitable hardness to withstand the forces of an archwire without distorting the slot.

It is therefore an object of the present invention to provide a new and improved orthodontic appliance in the form of an orthodontic bracket that includes a horizontally opening rectangular archwire slot, and a closed archwire slot capable of allowing crown tipping, limiting root uprighting, and controlling torquing to treat patients with the Tip Edge® technique.

A further object of the present invention is to provide a new and improved orthodontic bracket that includes a horizontally opening archwire slot and a closed archwire slot, together with a vertical slot for accommodating an uprighting spring for producing tooth uprighting movements.

A still further object of the present invention is to provide a new and improved orthodontic bracket made of a front section of metal, ceramic or plastic, having a horizontally opening rectangular archwire slot, and a rear section of a suitable plastic resin molded to the front section and configured to define a closed archwire slot.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 3 is a top plan view of the bracket of FIG. 1;

FIG. 4 is a side elevational view of the bracket of FIG. 1;

FIG. 5 is a vertical sectional view of the bracket of FIG. 3 and taken substantially along line 5-5 thereof;

FIG. 6 is a front elevational view of the bracket of FIG. 1;

FIG. 7 is a horizontal view of the bracket taken along line 7-7 of FIG. 4;

DETAILED DESCRIPTION OF THE INVENTION

Figure 1:
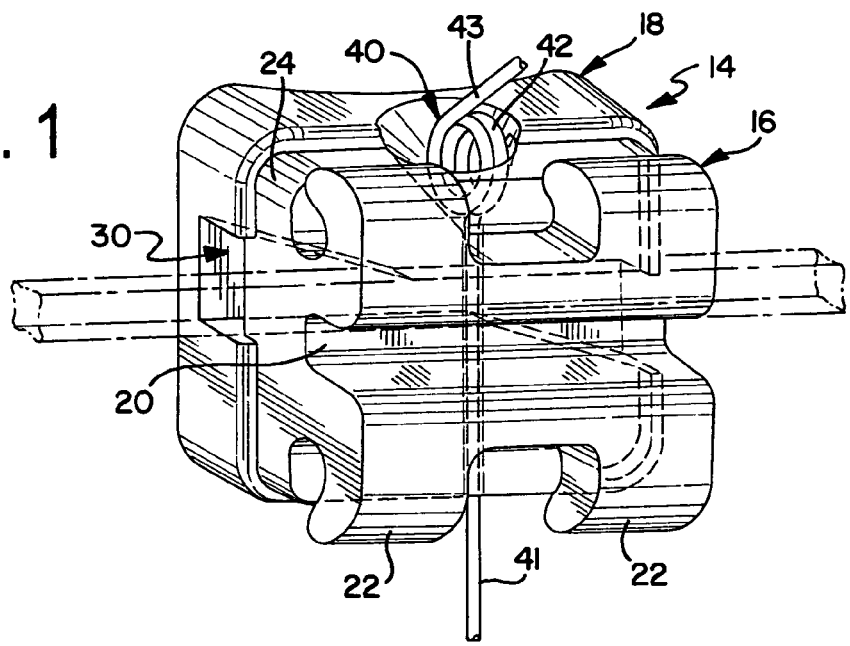
FIG. 1 is a front perspective view of the bracket according to the present invention showing in dotted lines the closed archwire slot and in phantom a rectangular archwire in the closed slot, and illustrating a partially fragmentary view of an uprighting spring.

The bracket of the present invention provides a combination bracket that includes a horizontally open rectangular slot for rectangular archwire to be used in connection with the usual straight-wire technique, or other edgewise techniques, and a closed archwire slot to be used in connection with the Tip Edge® technique wherein the closed slot includes means for coacting with the archwire to allow crown tipping, limit root uprighting to a predetermined angulation, and to control torquing. The standard horizontally opening archwire slot for rectangular archwire controls tip, torque and rotation. With respect to the horizontally opening archwire slot, it may or may not include single tie wings or double tie wings. The tie wings may be tied together to provide rigidity, or they may be separated as in the standard type of edgewise bracket. Moreover, with respect to the horizontally opening edgewise slot, it may be provided with means for closing the slot without the use of ligatures wherein it would be a self-ligating bracket. Where tie wings are provided, ligatures of the usual type may be used to retain the archwire in the slot such as the standard elastic ligatures or the standard wire tie ligatures.

Inasmuch as the bracket of the invention includes a horizontally opening archwire slot together with a closed archwire slot, the bracket may be constructed of two parts or sections permanently joined during manufacture, wherein the front or buccolabial part or section forming the open archwire slot may be made of the usual stainless steel, ceramic or plastic material, and the rear or lingual part or section would be molded of a suitable plastic resin to the backside of the first part and which would constitute the base of the bracket for bonding to a tooth. The rear section would also be configured during molding to define the closed archwire slot behind the main open archwire slot. Preferably, the rear section will be of a suitable plastic resin, such as an acrylic, which would be able to withstand any archwire forces that would exist between the bracket slot and the archwire during treatment and the application of forces to the bracket.

In this regard, the acrylic molded section would have built into its shape not only the arcuate bonding surface compatible with the tooth for which it is designed so that it would fit properly on a tooth, but also the tip, torque and rotation values that are intended to be incorporated into the bracket. In this respect, the bracket, which would define the horizontally opening rectangular slot, may be of a generic form for molding to a base having the particular prescription values.

Referring now to the drawings, the first embodiment of the invention is shown in FIGS. 1 to 7, and second and third embodiments of the invention are shown in FIGS. 8 to 11. The difference between the embodiments is in the structure of the front section of the bracket that defines the horizontally opening rectangular archwire slot as hereafter explained.

Referring now particularly to the embodiment of FIGS. 1 to 7, the bracket is generally designated by the numeral 14 and includes a front or buccolabial section or part 16 and a rear or lingual section or part 18.

Figure 8:
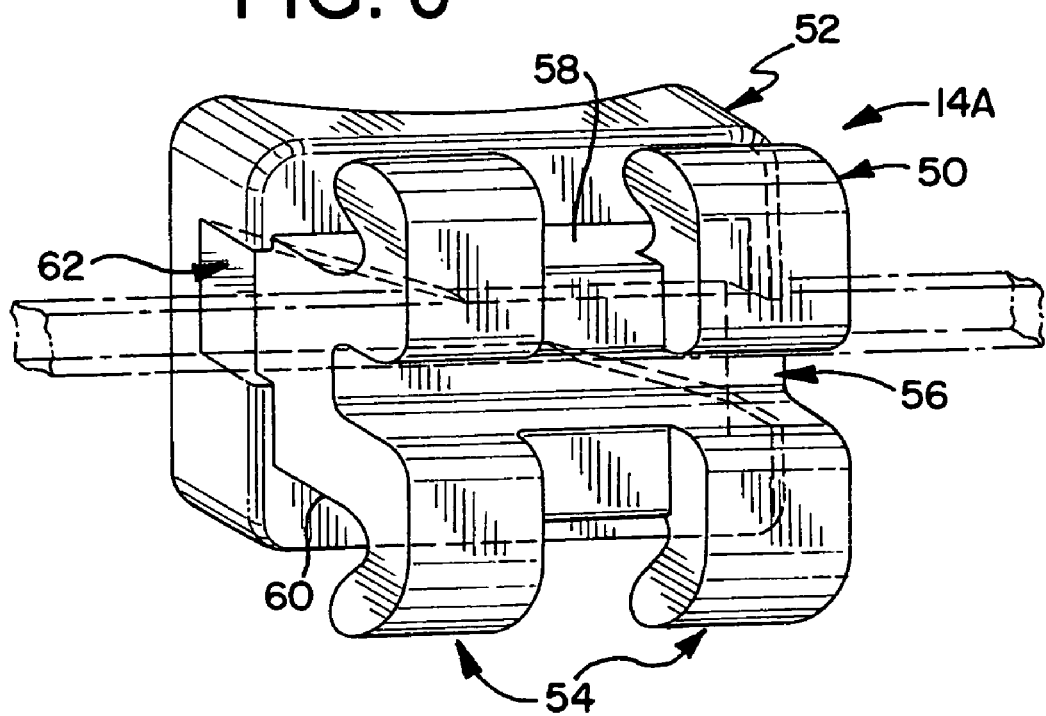
FIG. 8 is a modification of the invention and differs from the embodiment of FIGS. 1 to 7 in that the tie wing tips are spaced apart and not tied together, no vertical slot is provided, and the base of the front section does not include an enlarged portion.
Figure 9:
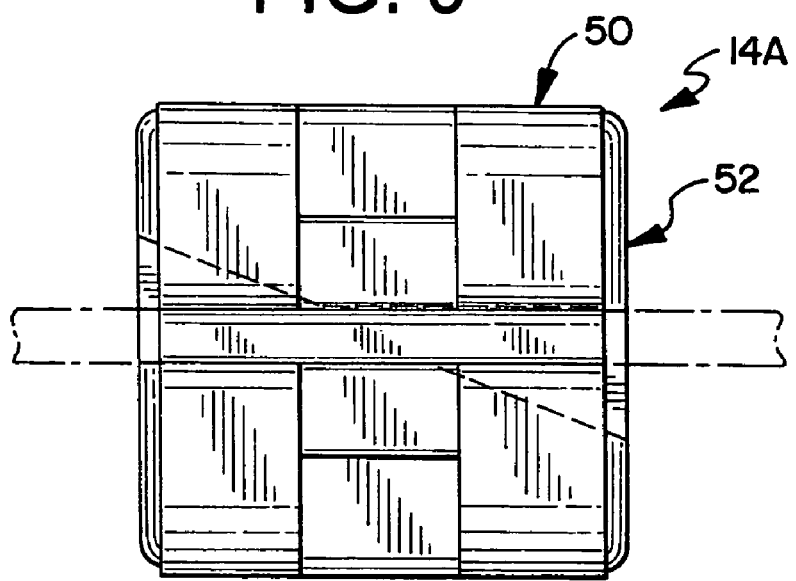
FIG. 9 is a front elevational view of the embodiment of FIG. 8.

The front section 16 of the embodiment illustrated is formed by any suitable method to define the horizontally opening rectangular archwire slot 20 adapted to coact with a main rectangular aligning archwire and twin tie wings 22. Such parts made of metal may be machined or cast, while parts made of ceramic or plastic are usually molded. Each tie wing includes dual opposed tips or ears for receiving a ligature to retain the archwire in the archwire slot. With respect to the embodiment disclosed in FIGS. 1 to 7, the tie wing tips are interconnected with each other by means of a horizontal reinforcing bar. However, it should be appreciated that the front section need not include the reinforcing bar and therefore define spaced apart tie wings at the buccolabial face, as shown in the embodiment of FIGS. 8 and 9. Moreover, it should be appreciated that the front section could merely be formed to have a single tie wing. The ligatures may be of wire or elastic in accordance with the desires or the orthodontist. Additionally, it should be appreciated that the front section could have a form of a self-ligating slot wherein additional mechanism and means would be provided to open and close the slot without the need for ligatures to retain the archwire in the slot. In all of the potential configurations, the front section would include a horizontally opening rectangular archwire slot for receiving a rectangular archwire particularly where the bracket would be used to practice the edgewise or straight-wire technique. However, it should be appreciated that a round wire could be used in some stages of treatment in the rectangular archwire slot if so desired by a particular orthodontist.

The front section 16 also includes an enlarged lingual base portion 24 to which the lingual section 18 would be molded. In the embodiment of FIGS. 1 to 7, the portion 24 is nearly as high as the tips of the tie wings and defines with the tie wings upper and lower cutouts 26 and 28 in which the ligatures are received when they are applied to the bracket for retaining an archwire in the horizontally opening rectangular archwire slot 20. The backside of the base 24 is substantially flat although, as will be explained below, it includes a vertically extending groove to coact with the lingual section 18 for defining a vertical slot to receive the tail of an uprighting spring as illustrated in the drawings.

Figure 2:
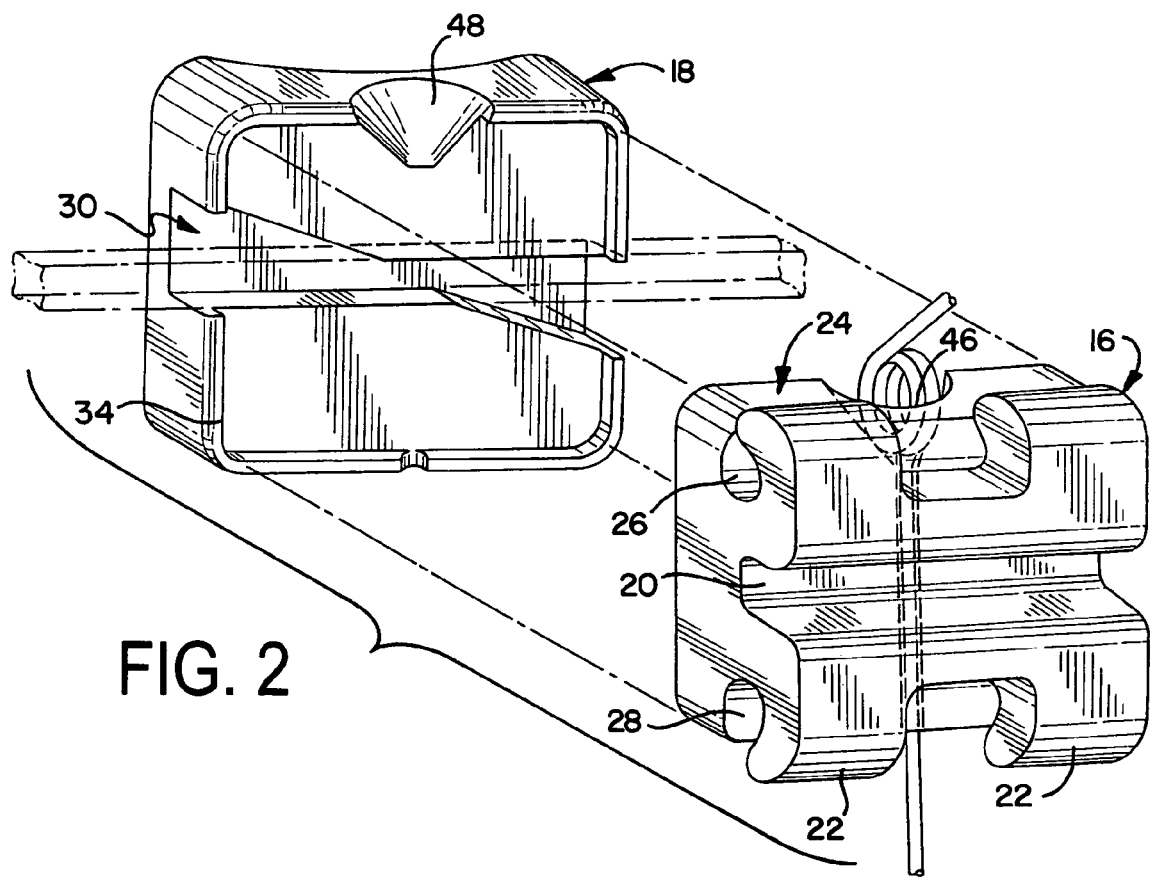
FIG. 2 is an exploded view of the bracket of FIG. 1 to illustrate the method of making the bracket wherein the base, which includes the inner archwire slot, may be configured of a suitable plastic resin and then molded onto the front section of the bracket.

While the lingual section 18 is shown separated from the buccolabial section 16 in FIG. 2, it will be appreciated that when the bracket is fully constructed it will be molded onto the buccolabial section and be integral therewith. As previously mentioned, the front or buccolabial section 16 of the bracket may be made of any suitable material, such as metal and particularly stainless steel, ceramic, plastic, or any combination thereof. Further, it may be of a standard sized part inasmuch as tip, torque and rotation values in accordance with any prescription can be built into the rear or lingual section 18.

The lingual section 18 of the bracket 14 is preferably formed of a suitable plastic resin, such as an acrylic, and molded onto the front section 16 of the bracket during the manufacture of the bracket. Any suitable acrylic or equivalent material may be used to mold the rear section onto the buccolabial section as long as it has sufficient strength to withstand the forces imparted relative to the archwire slot formed in the base section without deforming. Preferably, the archwire slot, generally designated 30, has a configuration as disclosed in U.S. Pat. Nos. 4,877,398 and 5,125,832 as above mentioned, which is configured to accommodate crown-tipping functions, root-uprighting functions, and torquing functions, in accordance with the Tip Edge® technique. For purposes of clarity, the disclosures in these patents are incorporated by reference. When viewed from the front, as generally seen in FIG. 2, the slot generally has a bow-tie shape. The slot generally includes opposed surfaces defined by angular segments which coact to define fulcrums about which the bracket can tip relative to the archwire. A standard rectangular archwire is preferably used in the slot 30, although it should be appreciated that a round archwire may be used in that slot for certain treatment phases as chosen by the orthodontist. The ability to provide the crown tipping and root uprighting functions facilitates the movement of teeth along the archwire to close spaces.

It will be appreciated that the archwire slot formed in the lingual section 18 in coaction with the rear surface of the base 24 of the buccolabial section 16 is a closed archwire slot that does not require any ligatures to retain the archwire in the slots of these brackets. The archwire is merely threaded through the slots of the various brackets when it is desired to utilize the Tip Edge® slot 30 in the base. With this in mind it should be appreciated that the orthodontist would have the option to use the horizontally opening rectangular archwire slot or to use the Tip Edge® slot during various phases of orthodontic treatment of a patient.

It should be further recognized that while as above mentioned both round and/or rectangular archwires may be used in either of the slots 20 or 30, the type of wire may vary depending upon the desired treatment of an orthodontist. For example, the wire may be stiff or it may be highly yieldable, such as a nickel titanium wire.

As seen in FIGS. 1 to 7, the lingual section 18 is preferably sized overall slightly larger than the base 24 of the buccolingual section 16 in order to provide an overlapping lip 34 that overlaps the base 24 to enhance the connection between the sections 16 and 18. As also seen in the drawings, the lingual surface of the lingual section 18 defines an arcuate surface 36 formed to conform with the buccolabial face of a tooth when bonding the bracket to a tooth. The arcuate shape may vary depending upon which tooth the bracket is to be mounted. Additionally, the arcuate face 36 would preferably have a roughened surface of any suitable type in order to enhance its gripping action with any bonding material that is used to attach the bracket or bond the bracket to a tooth.

The bracket 14 preferably includes a vertical slot for receiving the tail of a standard uprighting spring, as seen in the drawings. An uprighting spring 40 is shown with a tail 41 that extends through a vertical slot 44. The uprighting spring also includes a head or coil section 42 and a lever arm 43 for connecting to the archwire. In the embodiment illustrated, the vertical slot 44 is formed by a vertical groove in the rear face of the base 24 of the front section 16 and the front flat face of the back section 18. Further, the upper end of the front section 16 is provided with a notch 46 that coacts with a notch 48 in the back section 18 to define a recess for the head 42 of the uprighting spring to essentially hide the uprighting spring from the buccal or labial side. It will be appreciated that the tail 41 of the uprighting spring may be clipped off or bent over backward to anchor the uprighting spring in the vertical slot. The uprighting spring would only be used during certain aspects of the orthodontic treatment of a patient where an uprighting function would be desired.

Accordingly, it will be appreciated that during the manufacture of the bracket the lingual section 18 will be molded onto the front section 16 to provide a bracket having a horizontally opening rectangular archwire slot and a closed mesiodistally extending Tip Edge® archwire slot as well as a vertical slot for an uprighting spring. Thus, any desired prescription may be incorporated into a bracket by adjusting the formation of the lingual section when it is molded onto the buccolabial section.

Figure 10:
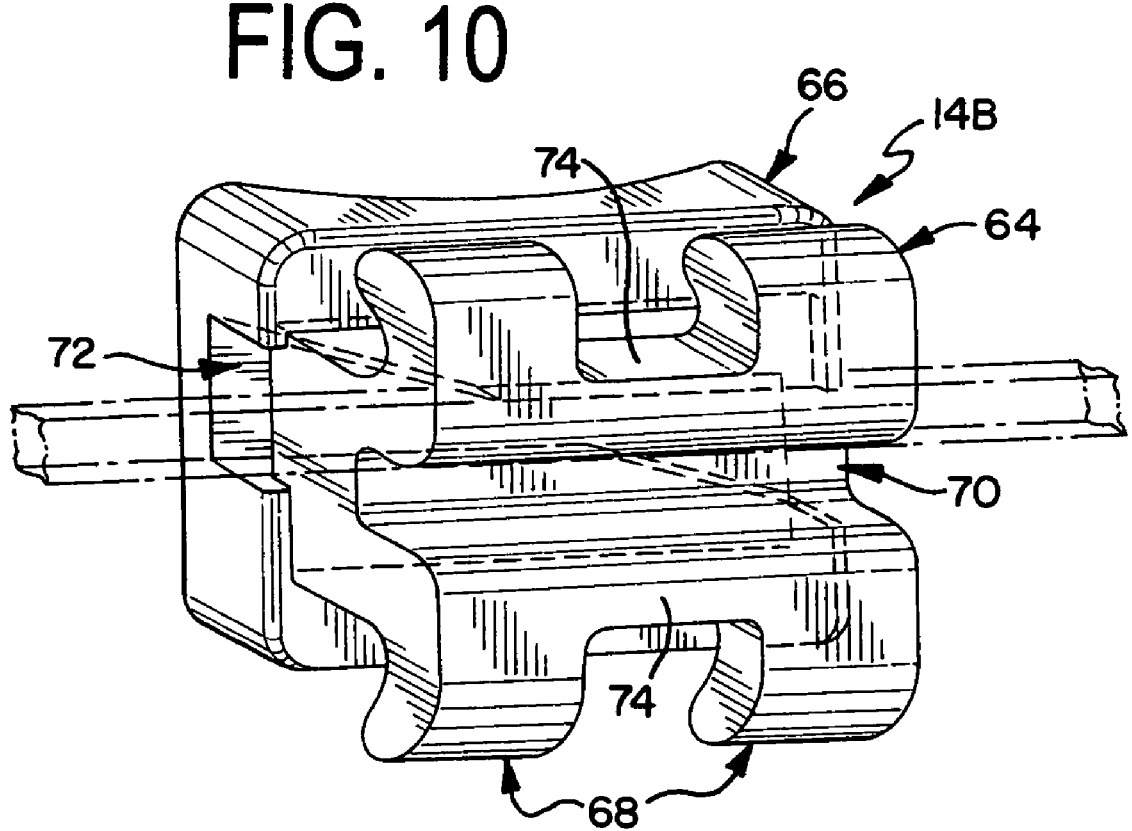
FIG. 10 is a further modification of the invention which differs from the embodiment of FIGS. 8 and 9 in that the tie wing tips are connected at the front face of the bracket with reinforcing bars.
Figure 11:
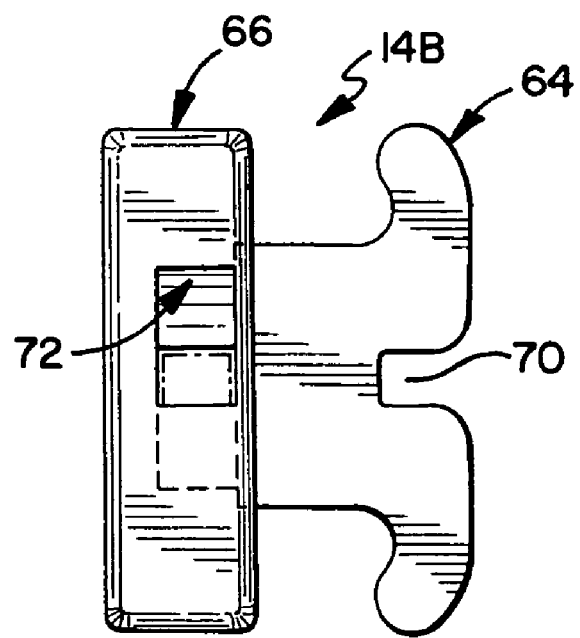
FIG. 11 is an end elevational view of the embodiment of FIG. 10.

The embodiments of FIGS. 8 to 11 are preferred as the front section differs in not including an enlarged portion behind the tie wing tips. Moreover, the embodiment of FIGS. 8 and 9 differs from the embodiment of FIGS. 1 to 7 in that it includes a typical twin tie wing configuration wherein the twin tie wing configuration allows each of the tie wings to be projecting from the base of the bracket. FIGS. 10 and 11 show the same embodiment as FIGS. 8 and 9 except for the reinforcing bar that extends between the upper and lower tie wing tips. Further, while the embodiments of FIGS. 8 and 9, 10 and 11 do not include a vertical slot, it should be appreciated that they could be structured with a vertical slot as in the embodiment of FIGS. 1 to 7, and that the vertical slot would be essentially disposed between the horizontally open rectangular archwire slot and the Tip Edge® slot. The vertical slot may be formed in the front section or the rear section.

The embodiment shown in FIGS. 8 and 9 is generally indicated by numeral 14A and includes a front section 50 and a rear or lingual section 52. The front or buccolabial section 50 includes spaced apart tie wings 54 which differ from the tie wing configuration of FIGS. 1 to 7 in that the tie wings are not connected together by a reinforcing bar at the upper and lower tie wing tips or ears. Between the tie wing tips a horizontally opening rectangular archwire slot 56 is defined and of the same form as in the embodiment of FIGS. 1 to 7 for receiving particularly in the final stages of treatment a rectangular archwire. As above mentioned, the base of the front section 50 differs from the base of the front section in the embodiment of FIGS. 1 to 7 in that it does not include an enlarged portion to which the base section is molded. Further, the base extends straight back or lingually from the bottom of the areas that would receive a ligature, as seen in FIGS. 8 and 9, to define upper and lower horizontally extending faces 58 and 60.

The rear or lingual section 52 is molded onto the backside of the front section 50 in substantially the same manner as the rear section is molded onto the front section in the embodiment of FIGS. 1 to 7 and configured to include a Tip Edge® slot 62 much like the Tip Edge® slot that is formed in the rear section of the embodiment of FIGS. 1 to 7. A rectangular archwire is shown in phantom in the Tip Edge® slot 62. As with respect to the first embodiment, the rear section is molded of a suitable acrylic of such a hardness that it can receive and bear the forces of an archwire during treatment of a patient without distortion of the Tip Edge® slot. As in the first embodiment, the orthodontist would have the option to use the bracket by threading a wire through the Tip Edge® slot for performing the Tip Edge® technique or by using a rectangular archwire for engagement with the horizontally opening rectangular archwire slot 56 in the front section particularly for performing the standard straight-wire or edgewise technique. While the final stages of treatment can be completed by use of either of the archwire slots, it would be appreciated that use of the horizontally opening archwire slot would generally be preferred.

Moreover, it would be appreciated with respect to this embodiment as in the embodiment of FIGS. 1 to 7 rectangular or round archwires may be used whether of the standard stiffness or of the super flexible type depending upon the phase of treatment desired by the orthodontist.

The modified bracket shown in FIGS. 10 and 11 is generally indicated by the numeral 14B and includes a front or buccolabial section 64 and a rear or lingual section 66. The front section likewise includes a pair of tie wings 68 having upper or lower tie wing tips or ears and a horizontally opening rectangular archwire slot 70. The rear section 66 includes a Tip Edge® archwire slot 72 and the rear section is molded to the back of the front section in the same manner as in the embodiment of FIGS. 10 and 11. The molding overlaps at least a part of the rear section in order to obtain a secure connection and provide an integral bracket with a base. Likewise, the acrylic base would be formed at the lingual face to fit on a particular tooth and to include built-in tip, torque and rotation values, particularly for the horizontally open archwire slot. This embodiment differs from the embodiment of FIG. 8 only in that the tie wing tips are connected at the buccolabial face with reinforcing bars 74 much like the embodiment of FIGS. 1 to 7. The base of the front section 64 is formed in the same manner as the base of the front section 50 in FIGS. 8 and 9, and the front section may be of any suitable material such as stainless steel, ceramic or plastic.

The function of the embodiment of FIGS. 10 and 11 is substantially identical to the function of FIGS. 8 and 9 in that an orthodontist may choose to use either the Tip Edge® slot 72 or the horizontally opening rectangular slot 70 during treatment of a patient in accordance with the desired stage of treatment.

It should also be appreciated that while the configuration of the brackets in the embodiments illustrated as seen from the labial and/or mesiodistal views are somewhat square in overall shape. They may be rhomboidally shaped from either of those views in order to follow certain prescription specifications. Also, as mentioned with respect to the embodiment of FIGS. 1 to 7, the configuration of the embodiments of FIGS. 8 to 11 could be such as to include means for defining the horizontally opening archwire slot in the front section to be self-ligating, thereby eliminating the necessity of using ligatures on the front section in order to retain the archwire in the front archwire slot.

It will be understood that modifications and variations may be effected without departing from the scope of the novel concepts of the present invention, but it is understood that this application is to be limited only by the scope of the appended claims.

The invention claimed is:

1. An orthodontic bracket comprising:
a horizontally opening archwire slot having directly opposed gingival and occlusal parallel faces for receiving a main aligning rectangular archwire for controlling tip, torque and rotation to perform the edgewise or straight-wire technique, and
a closed mesiodistally extending archwire slot separate from said horizontally opening archwire slot for receiving optionally and independently from said first slot a main aligning archwire to perform the technique of using the bracket to accommodate crown tipping, root uprighting, and torquing functions to close a space between adjacent teeth and to upright and/or torque a tooth to a predetermined position, said closed slot including means coacting with an archwire to allow crown tipping, limit root uprighting to a predetermined angulation, and control torquing, said closed slot means including diagonally opposed spaces and fulcrums to provide crown tipping and root uprighting functions to close a space, and diagonally opposed stop means to provide final torquing and uprighting functions, whereby said horizontally opening and closed archwire slots are used independently and exclusively of each other.

2. The bracket of claim 1, wherein said closed slot is lingual to said horizontally opening archwire slot.

3. The bracket of claim 2, which further includes twin tie wings for receiving a ligature to retain an archwire in said horizontally opening archwire slot.

4. The bracket of claim 3, which further includes a vertical slot for receiving the tail of an uprighting spring.

5. The bracket of claim 4, wherein the vertical slot is disposed lingual to said horizontally opening archwire slot.

6. The bracket of claim 4, wherein said bracket further includes a recess at one end of the vertical slot for receiving the head of an uprighting spring.

7. The bracket of claim 1, which further comprises a front section of metal, ceramic or plastic in which said horizontally opening archwire slot is disposed, and a rear section of plastic molded onto the front section in which said closed slot is disposed.

8. In an orthodontic system for applying corrective forces to teeth of an arch including centrals, laterals, cuspids and bicuspids, orthodontic brackets on the centrals, laterals, cuspids and bicuspids, each bracket including a horizontally opening archwire slot having directly opposed gingival and occlusal parallel faces for receiving a main rectangular archwire for controlling tip, torque and rotation to perform the edgewise or straight-wire technique, and a substantially passive rectangular or square archwire in said slot,
the improvement in the brackets which comprise:
each bracket further including a closed mesiodistally extending archwire slot independent from and separate from said horizontally opening slot for receiving optionally a main aligning archwire to perform the technique of using the bracket to accommodate crown tipping, root uprighting, and torquing functions to close a space between adjacent teeth and to upright and/or torque a tooth to a predetermined position, said closed slot having means for permitting crown tipping, limit root uprighting to a predetermined angulation and control torquing, and being separate from the horizontally opening archwire slot, said closed slot means including diagonally opposed spaces and fulcrums to provide crown tipping and root uprighting functions to close a space, and diagonally opposed stop means to provide final torquing and uprighting functions, whereby said horizontally opening and closed archwire slots are used independently and exclusively of each other.

9. The brackets of claim 8, wherein the closed slot of each bracket is lingual to said archwire slot.

10. The brackets of claim 9, wherein each bracket further includes twin tie wings for receiving a ligature to retain an archwire in said horizontally opening archwire slot.

11. The brackets of claim 10, wherein each bracket further includes a vertical slot for receiving an uprighting spring.

12. The brackets of claim 11, wherein the vertical slot is disposed lingual to said horizontally opening archwire slot.

13. The brackets of claim 11, wherein each bracket further includes a recess at the upper end of the vertical slot for receiving the head of the uprighting spring.

14. An orthodontic bracket comprising:
a front section of metal, ceramic or plastic, and having a horizontally opening archwire slot with directly opposed gingival and occlusal parallel faces for receiving a main aligning rectangular archwire for controlling tip, torque and rotation to perform the edgewise or straight-wire technique,
and a rear section of plastic molded onto the front section and having a closed mesiodistally extending slot independent of and separate from said horizontally opening archwire slot, for receiving optionally a main aligning archwire to perform the technique of using the bracket to accommodate crown tipping, root uprighting, and torquing functions to close a space between adjacent teeth and to upright and/or torque a tooth to a predetermined position, said closed slot including means coacting with an archwire to allow crown tipping, limit root uprighting to a predetermined angulation, and control torquing, said closed slot means including diagonally opposed spaces and fulcrums to provide crown tipping and root uprighting functions to close a space, and diagonally opposed stop means to provide final torquing and uprighting functions, whereby said horizontally opening and closed archwire slots are used independently and exclusively of each other.

15. The bracket of claim 14, wherein said closed slot is lingual to said archwire slot.

16. The bracket of claim 15, which further includes a plurality of tie wings for receiving a ligature to retain an archwire in said horizontally opening archwire slot.

17. The bracket of claim 16, which further includes a vertical slot for receiving the tail of an uprighting spring.

18. The bracket of claim 17, wherein the vertical slot is disposed lingual to said horizontally opening archwire slot.

19. The bracket of claim 17, wherein said bracket further includes a recess at one end of the vertical slot for receiving the head of an uprighting spring.

\* \* \* \* \*